United States Patent
Bar

(10) Patent No.: US 9,278,924 B2
(45) Date of Patent: Mar. 8, 2016

(54) 5-NONYLOXYTRYPTAMINE AND RELATED INTRACELLULAR PH ACIDIFIERS FOR THE TREATMENT AND PREVENTION OF CANCER

(71) Applicant: THE JOHNS HOPKINS UNIVERSITY, Baltimore, MD (US)

(72) Inventor: Eli Eliyahu Bar, Washington, DC (US)

(73) Assignee: The Johns Hopkins University, Baltimore, MD (US)

( * ) Notice: Subject to any disclaimer, the term of this patent is extended or adjusted under 35 U.S.C. 154(b) by 127 days.

(21) Appl. No.: 14/353,911

(22) PCT Filed: Oct. 25, 2012

(86) PCT No.: PCT/US2012/061839
§ 371 (c)(1),
(2) Date: Apr. 24, 2014

(87) PCT Pub. No.: WO2013/063216
PCT Pub. Date: May 2, 2013

(65) Prior Publication Data
US 2014/0296278 A1    Oct. 2, 2014

Related U.S. Application Data

(60) Provisional application No. 61/551,022, filed on Oct. 25, 2011.

(51) Int. Cl.
| | |
|---|---|
| *A61K 31/4045* | (2006.01) |
| *C07D 209/14* | (2006.01) |
| *A61K 45/06* | (2006.01) |
| *C07D 209/16* | (2006.01) |

(52) U.S. Cl.
CPC .......... *C07D 209/14* (2013.01); *A61K 31/4045* (2013.01); *A61K 45/06* (2013.01); *C07D 209/16* (2013.01)

(58) Field of Classification Search
None
See application file for complete search history.

(56) References Cited

U.S. PATENT DOCUMENTS

| | | |
|---|---|---|
| 2002/0173511 A1 | 11/2002 | Wurtman et al. |
| 2005/0080084 A1 | 4/2005 | Stephenson |
| 2006/0009512 A1 | 1/2006 | Curwen et al. |
| 2010/0137194 A1 | 6/2010 | Lawrence et al. |

FOREIGN PATENT DOCUMENTS

WO     2010-077839  A1    7/2010

OTHER PUBLICATIONS

Siddiqui et al. (Journal of Urology, 176: 1648-1653, 2006).*

* cited by examiner

*Primary Examiner* — Bong-Sook Baek
(74) *Attorney, Agent, or Firm* — Johns Hopkins Technology Transfer

(57) ABSTRACT

Provided herein are compositions for lowering intracellular pH in a cell or population of cells from a subject comprising contacting the cell or population of cells with a therapeutically effective amount of 5-nonyloxytryptamine or a pharmaceutically acceptable salt, solvate, stereoisomer, or derivatives thereof. These compounds are useful for acidification of cells, including cancer cells, which induces apoptosis and cell necrosis. Methods of use of these compounds, including in pharmaceutical compositions in conjunction with other biologically active agents, in treatment of cancers, including glioblastoma and related neuronal cancers are also included.

6 Claims, 5 Drawing Sheets

5-NONYLOXYTRYPTAMINE AND RELATED INTRACELLULAR PH ACIDIFIERS FOR THE TREATMENT AND PREVENTION OF CANCER

CROSS-REFERENCE TO RELATED APPLICATIONS

This application is a 35 U.S.C. §371 U.S. national entry of International Application PCT/US2012/061839, having an international filing date of Oct. 25, 2012, which claims the benefit of U.S. Provisional Application No. 61/551,022, filed Oct. 25, 2011, the content of each of the aforementioned applications is herein incorporated by reference in their entirety.

BACKGROUND OF THE INVENTION

Glioma is a common type of primary brain tumor, accounting for about 33% of these tumors. Gliomas originate in the glial cells in the brain. Glial cells are the tissue that surrounds and supports neurons in the brain.

These tumors arise from three different types of cells that are normally found in the brain: astrocytes, oligodendrocytes, and ependymal cells. Gliomas are called intrinsic brain tumors because they reside within the substance of the brain and often intermix with normal brain tissue.

There are different grades of gliomas; however, they are most often referred to as "low-grade" or "high-grade" gliomas. The low or high grade designation reflects the growth potential and aggressiveness of the tumor.

Glioblastoma multiforme (GBM) is the most common and most aggressive malignant primary brain tumor in humans, involving glial cells and accounting for 52% of all functional tissue brain tumor cases and 20% of all intracranial tumors. Despite being the most prevalent form of primary brain tumor, GBM incidence is only 2-3 cases per 100,000 people in Europe and North America. According to the WHO classification of the tumors of the central nervous system, the standard name for this brain tumor is "glioblastoma"; it presents two variants: giant cell glioblastoma and gliosarcoma.

Treatment can involve chemotherapy, radiation, radiosurgery, corticosteroids, antiangiogenic therapy, surgery and experimental approaches such as gene transfer.

With the exception of the brainstem gliomas, glioblastoma has the worst prognosis of any central nervous system (CNS) malignancy, despite multimodality treatment consisting of open craniotomy with surgical resection of as much of the tumor as possible, followed by concurrent or sequential chemoradiotherapy, antiangiogenic therapy with bevacizumab, gamma knife radiosurgery, and symptomatic management with corticosteroids. Prognosis is very poor, with a median survival time of approximately 12-14 months and is almost invariably fatal.

The current therapeutic modality for glioma includes surgery, radiotherapy, and chemotherapy. The most widely used drugs are carmustine, lomustine, vincristine, procarbazine, carboplatin, etoposide and irinotecan. Neoadjuvant or adjuvant therapy with these drugs was shown to prolong disease-free survival but not overall survival. Recently, concurrent temozolomide and radiotherapy has become the new standard of care for patients diagnosed with GBM, prolonging survival from 12 months to 15 months.

However, there still exists a pressing need for novel treatment modalities to treat and cure GBM and related cancers,

SUMMARY OF THE INVENTION

In accordance with one or more embodiments, the present invention provides the use of 5-nonyloxytryptamine and other intracellular pH acidifiers for the treatment and prevention of cancer. The compounds may be administered alone or combined with one or more agents selected from the group consisting of cytotoxic or cytostatic agents, surgery, and ionizing radiation.

In accordance with an embodiment, the present invention provides a method for lowering intracellular pH in a cell or population of cells from a subject comprising contacting the cell or population of cells with a therapeutically effective amount of a compound of formula I:

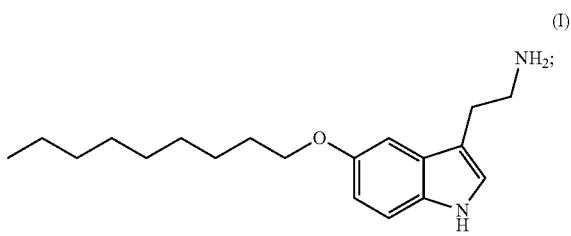 [SMILES: CCCCCCCCCOc1ccc2[nH]cc(CCN)c2c1]

or a pharmaceutically acceptable salt, solvate, stereoisomer, or derivative thereof.

In accordance with another embodiment the present invention provides a method for inducing apoptosis in a cell or population of cells from a subject comprising contacting the cell or population of cells with a therapeutically effective amount of a compound of formula I:

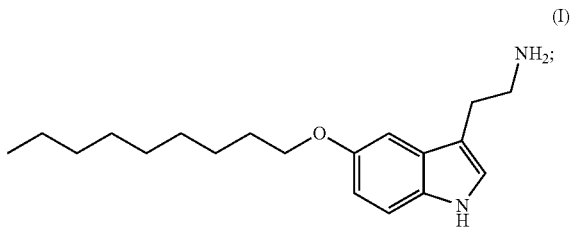

or a pharmaceutically acceptable salt, solvate, stereoisomer, or derivative thereof.

In accordance with a further embodiment, the present invention provides a method for treating cancer in a subject comprising administering to the subject a therapeutically effective amount of a compound of formula I:

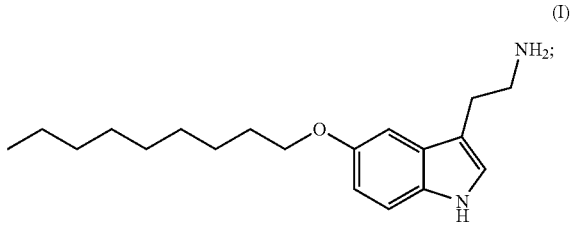 [SMILES: CCCCCCCCCOc1ccc2[nH]cc(CCN)c2c1]

or a pharmaceutically acceptable salt, solvate, stereoisomer, or derivative thereof.

In accordance with still another embodiment, the present invention provides a pharmaceutical composition comprising a therapeutically effective amount of a compound of formula I:

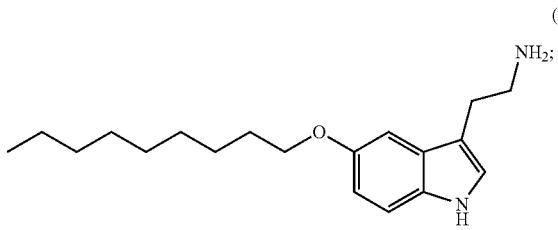

or a pharmaceutically acceptable salt, solvate, stereoisomer, or derivative thereof, and at least one additional chemotherapeutic compound in a pharmaceutically acceptable carrier.

In accordance with an embodiment, the present invention provides a method for treating cancer in a subject comprising administering to the subject a therapeutically effective amount of a pharmaceutical composition comprising a therapeutically effective amount of a compound of formula I:

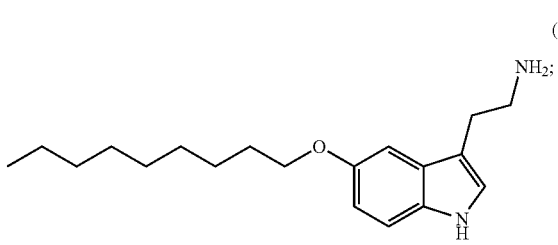

or a pharmaceutically acceptable salt, solvate, stereoisomer, or derivative thereof, and at least one additional chemotherapeutic compound in a pharmaceutically acceptable carrier.

DETAILED DESCRIPTION OF THE INVENTION

Figure 1:
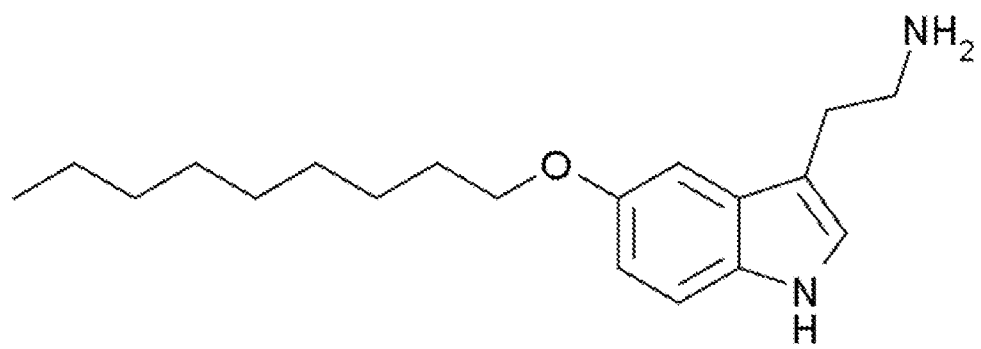
FIG. 1 illustrates the chemical structure of the lead compound of the embodiments of the present invention.

Alkaline intracellular pH is known to be required by cancer cells for proliferation and resistance to chemotherapy. The present inventors investigated methods to identify compounds that lower intracellular pH and thereby would inhibit cancer cell proliferation and increase cancer sensitivity to chemotherapy.

In accordance with still another embodiment, the present invention provides a pharmaceutical composition comprising a therapeutically effective amount of a compound of formula I:

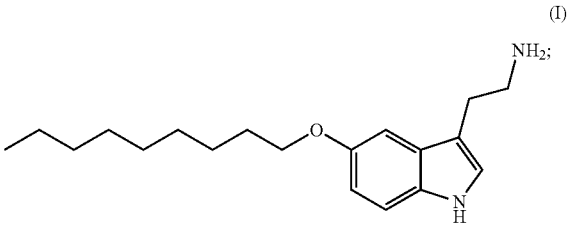 [SMILES: CCCCCCCCCOc1ccc2[nH]cc(CCN)c2c1]

or a pharmaceutically acceptable salt, solvate, stereoisomer, or derivative thereof, and at least one additional chemotherapeutic compound in a pharmaceutically acceptable carrier.

In accordance with an embodiment, the present invention provides a method for lowering intracellular pH in a cell or population of cells from a subject comprising contacting the cell or population of cells with a therapeutically effective amount of a compound of formula I:

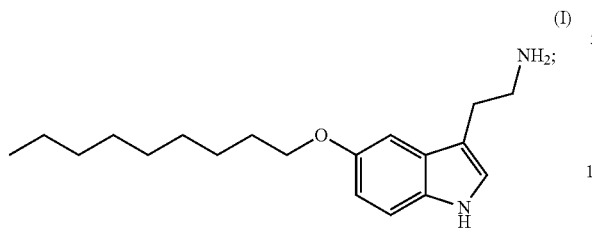

or a pharmaceutically acceptable salt, solvate, stereoisomer, or derivative thereof.

In another embodiment, the present invention provides a pharmaceutical composition comprising a compound, salt, solvate, or stereoisomer of any one of the compounds of Formula I, as set forth above, and at least one or more other anticancer compounds, and a pharmaceutically acceptable carrier.

In an embodiment, the present invention provides that the other anticancer compounds can be, for example, anticancer drugs from the following drug classes, including, but not limited to, antimitotics, antineoplastics, antimetabolites, and alkylating agents. Such classes of anticancer drugs are well known in the art.

Accordingly, included within the compounds of the present invention are the tautomeric forms of the disclosed compounds, isomeric forms including enantiomers, stereoisomers, and diastereoisomers, and the pharmaceutically-acceptable salts thereof. The term "pharmaceutically acceptable salts" embraces salts commonly used to form alkali metal salts and to form addition salts of free acids or free bases. Examples of acids which may be employed to form pharmaceutically acceptable acid addition salts include such inorganic acids as hydrochloric acid, sulphuric acid and phosphoric acid, and such organic acids as maleic acid, succinic acid and citric acid. Other pharmaceutically acceptable salts include salts with alkali metals or alkaline earth metals, such as sodium, potassium, calcium and magnesium, or with organic bases, such as dicyclohexylamine. Suitable pharmaceutically acceptable salts of the compounds of the present invention include, for example, acid addition salts which may, for example, be formed by mixing a solution of the compound according to the invention with a solution of a pharmaceutically acceptable acid, such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. All of these salts may be prepared by conventional means by reacting, for example, the appropriate acid or base with the corresponding compounds of the present invention.

Salts formed from free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For use in medicines, the salts of the compounds of the present invention should be pharmaceutically acceptable salts. Other salts may, however, be useful in the preparation of the compounds according to the invention or of their pharmaceutically acceptable salts.

In accordance with an embodiment, the present invention provides a pharmaceutical composition comprising a therapeutically effective amount of a compound of formula I:

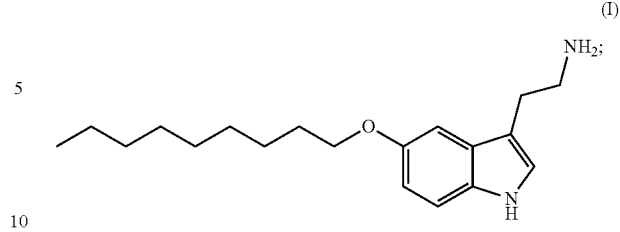

or a pharmaceutically acceptable salt, solvate, stereoisomer, or derivative thereof, and a pharmaceutically acceptable carrier, for use as a medicament, preferably for use in treating cancer in a subject, more preferably for use in treating glioblastoma in a subject.

In accordance with another embodiment, the present invention provides a pharmaceutical composition comprising a therapeutically effective amount of a compound of formula I:

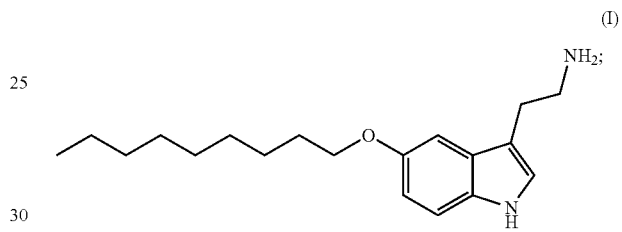

or a pharmaceutically acceptable salt, solvate, stereoisomer, or derivative thereof, and at least one additional chemotherapeutic compound in a pharmaceutically acceptable carrier, for use as a medicament, preferably for use in treating cancer in a subject, more preferably for use in treating glioblastoma in a subject.

In addition, embodiments of the invention include hydrates of the compounds of the present invention. The term "hydrate" includes but is not limited to hemihydrate, monohydrate, dihydrate, trihydrate and the like. Hydrates of the compounds of the present invention may be prepared by contacting the compounds with water under suitable conditions to produce the hydrate of choice.

In an embodiment, the pharmaceutical compositions of the present invention comprise the compounds of the present invention, for example, the compounds of Formula I, and/or their salts, solvates or stereoisomers thereof, and optionally, one or more other therapeutic agents, such as anticancer compounds, together with a pharmaceutically acceptable carrier.

In accordance with another embodiment, the present invention provides a pharmaceutical composition comprising a therapeutically effective amount of a compound of formula I:

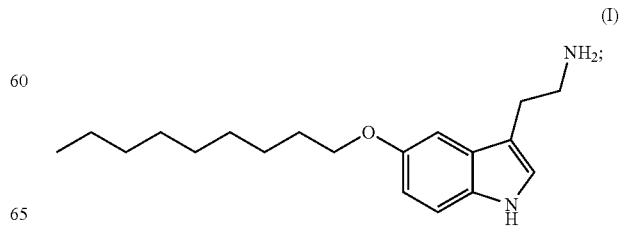

or a pharmaceutically acceptable salt, solvate, stereoisomer, or derivative thereof, and a pharmaceutically acceptable carrier, for use as a medicament, preferably for use in lowering intracellular pH in a cell or population of cells in a subject.

It will be understood that the cell or population of cells in the subject could be any cell, including for example, a cancer cell. In a preferred embodiment, the cell or population of cells being treated are neuronal cancer cells, such as glioblastoma cells.

Embodiments of the invention also include a process for preparing pharmaceutical products comprising the compounds. The term "pharmaceutical product" means a composition suitable for pharmaceutical use (pharmaceutical composition), as defined herein. Pharmaceutical compositions formulated for particular applications comprising the compounds of the present invention are also part of this invention, and are to be considered an embodiment thereof.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

As used herein, the term "subject" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

With respect to pharmaceutical compositions described herein, the pharmaceutically acceptable carrier can be any of those conventionally used, and is limited only by physicochemical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. Examples of the pharmaceutically acceptable carriers include soluble carriers such as known buffers which can be physiologically acceptable (e.g., phosphate buffer) as well as solid compositions such as solid-state carriers or latex beads. It is preferred that the pharmaceutically acceptable carrier be one which is chemically inert to the active agent(s), and one which has little or no detrimental side effects or toxicity under the conditions of use.

The carriers or diluents used herein may be solid carriers or diluents for solid formulations, liquid carriers or diluents for liquid formulations, or mixtures thereof.

Solid carriers or diluents include, but are not limited to, gums, starches (e.g., corn starch, pregelatinized starch), sugars (e.g., lactose, mannitol, sucrose, dextrose), cellulosic materials (e.g., microcrystalline cellulose), acrylates (e.g., polymethylacrylate), calcium carbonate, magnesium oxide, talc, or mixtures thereof.

For liquid formulations, pharmaceutically acceptable carriers may be, for example, aqueous or non-aqueous solutions, suspensions, emulsions or oils. Examples of non-aqueous solvents are propylene glycol, polyethylene glycol, and injectable organic esters such as ethyl oleate. Aqueous carriers include, for example, water, alcoholic/aqueous solutions, cyclodextrins, emulsions or suspensions, including saline and buffered media.

Examples of oils are those of petroleum, animal, vegetable, or synthetic origin, for example, peanut oil, soybean oil, mineral oil, olive oil, sunflower oil, fish-liver oil, sesame oil, cottonseed oil, corn oil, olive, petrolatum, and mineral. Suitable fatty acids for use in parenteral formulations include, for example, oleic acid, stearic acid, and isostearic acid. Ethyl oleate and isopropyl myristate are examples of suitable fatty acid esters.

Parenteral vehicles (for subcutaneous, intravenous, intraarterial, or intramuscular injection) include, for example, sodium chloride solution, Ringer's dextrose, dextrose and sodium chloride, lactated Ringer's and fixed oils. Formulations suitable for parenteral administration include, for example, aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Intravenous vehicles include, for example, fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions.

In addition, in an embodiment, the compounds of the present invention may further comprise, for example, binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate), buffers (e.g., Tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., cremophor, glycerol, polyethylene glycerol, benzalkonium chloride, benzyl benzoate, cyclodextrins, sorbitan esters, stearic acids), anti-oxidants (e.g., ascorbic acid, sodium metabisulfite, butylated hydroxyanisole), stabilizers (e.g., hydroxypropyl cellulose, hydroxypropylmethyl cellulose), viscosity increasing agents (e.g., carbomer, colloidal silicon dioxide, ethyl cellulose, guar gum), sweetners (e.g., aspartame, citric acid), preservatives (e.g., thimerosal, benzyl alcohol, parabens), lubricants (e.g., stearic acid, magnesium stearate, polyethylene glycol, sodium lauryl sulfate), flowaids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates), and/or adjuvants.

The choice of carrier will be determined, in part, by the particular compound, as well as by the particular method used to administer the compound. Accordingly, there are a variety of suitable formulations of the pharmaceutical composition of the invention. The following formulations for parenteral, subcutaneous, intravenous, intramuscular, intraarterial, intrathecal and interperitoneal administration are exemplary, and are in no way limiting. More than one route can be used to administer the compounds, and in certain instances, a particular route can provide a more immediate and more effective response than another route.

Suitable soaps for use in parenteral formulations include, for example, fatty alkali metal, ammonium, and triethanolamine salts, and suitable detergents include, for example, (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain from about 0.5% to about 25% by weight of the compounds in solution. Preservatives and buffers may be used. In order to minimize or eliminate irritation at the site of injection, such compositions may contain one or more nonionic surfactants, for example, having a hydrophile-lipophile balance (HLB) of from about 12 to about 17. The quantity of surfactant in such formulations will typically range from about 5% to about 15% by weight. Suitable surfactants include, for example, polyethylene glycol sorbitan fatty acid esters, such as sorbitan monoleate and the high molecular weight adducts of ethylene oxide with a hydrophobic base, formed by the condensation of propylene oxide with propylene glycol.

The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Injectable formulations are in accordance with the invention. The requirements for effective pharmaceutical carriers for injectable compositions are well-known to those of ordinary skill in the art (see, e.g., *Pharmaceutics and Pharmacy Practice*, J. B. Lippincott Company, Philadelphia, Pa., Banker and Chalmers, eds., pages 238-250 (1982), and *ASHP Handbook on Injectable Drugs*, Trissel, 15th ed., pages 622-630 (2009)).

For purposes of the invention, the amount or dose of the compounds, salts, solvates, or stereoisomers of any one the compounds of Formula I, as set forth above, administered should be sufficient to effect, e.g., a therapeutic or prophylactic response, in the subject over a reasonable time frame. The dose will be determined by the efficacy of the particular compound and the condition of a human, as well as the body weight of a human to be treated.

The dose of the compounds, salts, solvates, or stereoisomers of any one the compounds of Formula I, as set forth above, of the present invention also will be determined by the existence, nature and extent of any adverse side effects that might accompany the administration of a particular compound. Typically, an attending physician will decide the dosage of the compound with which to treat each individual patient, taking into consideration a variety of factors, such as age, body weight, general health, diet, sex, compound to be administered, route of administration, and the severity of the condition being treated. By way of example, and not intending to limit the invention, the dose of the compound can be about 0.001 to about 1000 mg/kg body weight of the subject being treated/day, from about 0.01 to about 100 mg/kg body weight/day, about 0.1 mg to about 10 mg/kg body weight/day.

Alternatively, the compounds of the present invention can be modified into a depot form, such that the manner in which the compound is released into the body to which it is administered is controlled with respect to time and location within the body (see, for example, U.S. Pat. No. 4,450,150). Depot forms of compounds can be, for example, an implantable composition comprising the compound and a porous or non-porous material, such as a polymer, wherein the compound is encapsulated by or diffused throughout the material and/or degradation of the non-porous material. The depot is then implanted into the desired location within the body and the compounds are released from the implant at a predetermined rate.

In one embodiment, the compounds of the present invention provided herein can be controlled release compositions, i.e., compositions in which the one or more compounds are released over a period of time after administration. Controlled or sustained release compositions include formulation in lipophilic depots (e.g., fatty acids, waxes, oils). In another embodiment the composition is an immediate release composition, i.e., a composition in which all or substantially all of the compound is released immediately after administration.

In yet another embodiment, the compounds of the present invention can be delivered in a controlled release system. For example, the agent may be administered using intravenous infusion, an implantable osmotic pump, a transdermal patch, or other modes of administration. In an embodiment, a pump may be used. In one embodiment, polymeric materials can be used. In yet another embodiment, a controlled release system can be placed in proximity to the therapeutic target, i.e., the brain, thus requiring only a fraction of the systemic dose (see, e.g., *Design of Controlled Release Drug Delivery Systems*, Xiaoling Li and Bhaskara R. Jasti eds. (McGraw-Hill, 2006)).

The compounds included in the pharmaceutical compositions of the present invention may also include incorporation of the active ingredients into or onto particulate preparations of polymeric compounds such as polylactic acid, polyglycolic acid, hydrogels, etc., or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance.

In accordance with an embodiment, the present invention provides a method for treating cancer in a subject comprising administering to the subject a therapeutically effective amount of a pharmaceutical composition comprising a therapeutically effective amount of a compound of formula I:

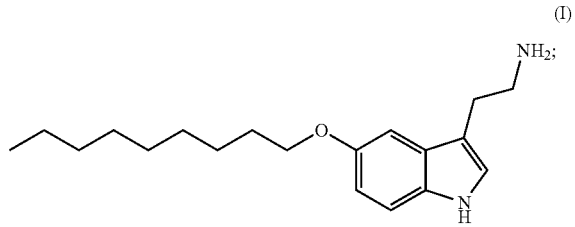 [SMILES: CCCCCCCCCOc1ccc2[nH]cc(CCN)c2c1]

or a pharmaceutically acceptable salt, solvate, stereoisomer, or derivative thereof, and at least one additional chemotherapeutic compound in a pharmaceutically acceptable carrier.

As used herein the term "pharmaceutically active compound" or "therapeutically active compound" means a compound useful for the treatment or modulation of a disease or condition in a subject suffering therefrom. Examples of pharmaceutically active compounds can include any drugs known in the art for treatment of disease indications. A particular example of a pharmaceutically active compound is a chemotherapeutic agent.

The term "chemotherapeutic agent" as well as words stemming therefrom, as used herein, generally includes pharmaceutically or therapeutically active compounds that work by interfering with DNA synthesis or function in cancer cells. Based on their chemical action at a cellular level, chemotherapeutic agents can be classified as cell-cycle specific agents (effective during certain phases of cell cycle) and cell-cycle nonspecific agents (effective during all phases of cell cycle). Without being limited to any particular example, examples of chemotherapeutic agents can include alkylating agents, angiogenesis inhibitors, aromatase inhibitors, antimetabolites, anthracyclines, antitumor antibiotics, monoclonal antibodies, platinums, topoisomerase inhibitors, and plant alkaloids.

Example 1

A small molecule drug screen was performed using the NINDS Clinical Compound Collection and the intracellular pH indicator Carboxy SNARF-1 (C-SNARF-1, Molecular Probes). Briefly, the GBM neurosphere cell line 020913 was triturated to a single cell suspension. Twenty-thousand cells were plated per well in a black-walled 96-well plate. Drugs were added at a final concentration of 2 µM per well. As a negative control, cells were plated with DMSO (vehicle) in triplicate; for normalization of the GSNARF-1 reaction, cells were plated with DMSO in an additional 3 wells (no SNARF control). After 24 hr, 2 µl GSNARF'-1 was added to each well except for the no SNARF control wells at a final concentration of 1.4 µM and incubated at room temperature for 10 minutes. The plate was then spun down at 190×g for 10 minutes, after which the media was removed and replaced with phenol red-free DMEM/F 12 media (Invitrogen). The plate was read using a BioTek microplate reader at 680 nm and then at 590 nm. To identify acidifying compounds, the ratio of the fluorescence intensities measured at the emission wavelengths of 680 nm and 590 nm was calculated for each well. All 680 nm/590 nm ratios were normalized to the average 680 nm/590 nm ratio of the no SNARF control wells. Drugs which lowered the intracellular pH by more than two standard deviations were further characterized. The present invention describes the characterization of one or more drugs, including, for example, 5-nonyloxytryptamine oxalate (5-NOTO), which tested positive in the screen.

Example 2

Figure 2:
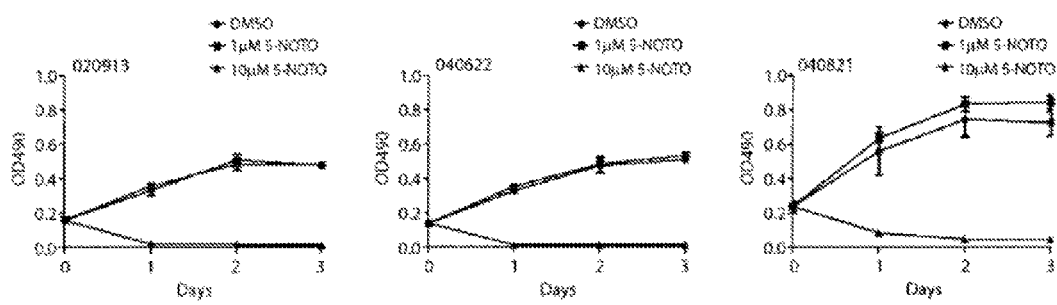
FIG. 2 depicts MTT growth assays for neurospheres treated with 5-NOTO. Cells were plated in 96-multiwell plates and treated with either DM50 (Control •) or 5-NOTO (at 1 uM ■ and 10 μM ▲). MTT reagent was added to indirectly measure viable cell mass at each time point. Absorbance was measured wt 490 nm using an Epoch Microplate Spectrophotometer (BioTek).

5-NOTO is a Potent Inhibitor of Cancer Cell Growth. To test the hypothesis that as a pH acidifier, 5-NOTO should reduce cell proliferation, we treated three independent GBM-derived neurosphere cell lines with DMSO (control), 1 µM, and 10 µM 5-NOTO for three days. Accumulation of viable cell mass was measured using MTT growth assay (Promega). Absorbance (A490) was measured using an Epoch Microplate Spectrophotometer (Biotek) at the indicated time points. It was found that 10 µM 5-NOTO inhibited the growth of all three neurosphere lines tested by more than 90% (FIG. 2). This result was very surprising as these GBM neurosphere lines have been shown to harbor high percentage of cancer stem-like cells which are considered to be highly resistant to conventional chemotherapy and radiation.

Example 3

Figure 3:
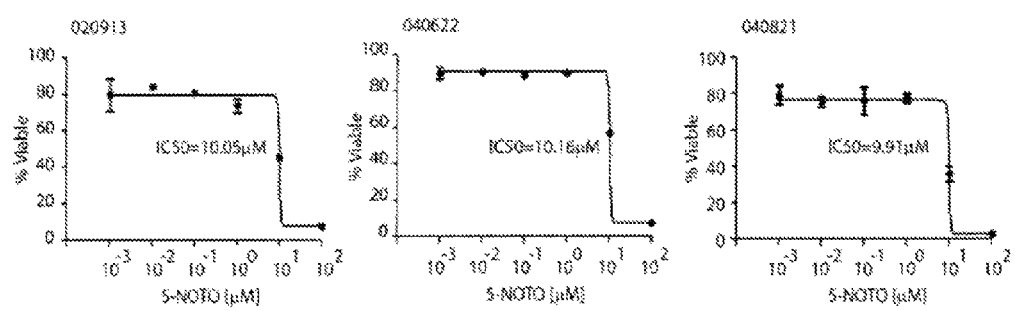
FIG. 3 shows the determination of $IC_{50}$ for 5-NOTO. Cells were treated for 48 hours with various concentrations of 5-NOTO and incubated for 48 hours in humidified incubator as which point, Guava Viacount reagent (Millipore) was used to assess the percentage of viable cells remaining in each treatment well. $IC_{50}$ (concentration of drug required for 50% reduction in cell viability) was calculated using Graphpad 5.0 software package. The respective $IC_{50}$ is indicated for each neurosphere line.

Determination of cytotoxic effects. We next sought to determine the concentration of 5-NOTO which is required to kill 50% of the cells (e.g. $IC_{50}$). Cells were plated in 24-well plates at 25,000 cells/well and treated for 48 hours with either DMSO (control) or various concentration of 5-NOTO (FIG. 2). Guava PCA flow cytometry system was used with the Guava Viawunt reagent (Millipore) to determine cell viability. Data was analyzed using GraphPad 5.0 software package. $IC_{50}$ was calculated using non linear regression. Importantly, all neurospheres tested showed an $IC_{50}$ of about 10 µM (FIG. 3). Careful analysis of the mechanism by which 5-NOTO induces cell death revealed that both apoptosis and necrosis were induced (FIG. 3).

Example 4

5-NOTO Induces Apoptosis in GBM Neurospheres. To ascertain that 5-NOTO induces apoptosis, cells were treated with DMSO (control), 1 µM, and 10 µM 5-NOTO for 24 hours at which point cells were processed for Annexin V apoptosis assay (Millipore), which is a simple and effective method to detect one of the earliest events in apoptosis, the externalization of phosphatidylserine in living cells. It was found that 10 µM 5-NOTO treatment resulted in dramatic increase in the apoptotic cell fraction with percentage increases from 10-20% in DMSO treated neurospheres to more than 60%, 70%, and 80% in 040622, 040821, and 020913, respectively. Higher levels of 5-NOTO (100 µM) eliminated the vast majority of viable cells (80-90%) 48 hours post treatment (Data not shown)). These sets of experiments clearly show that 5-NOTO induces apoptosis in Glioblastoma derived neurospheres and therefore holds great promise as a potential therapy.

Example 5

Figure 5:
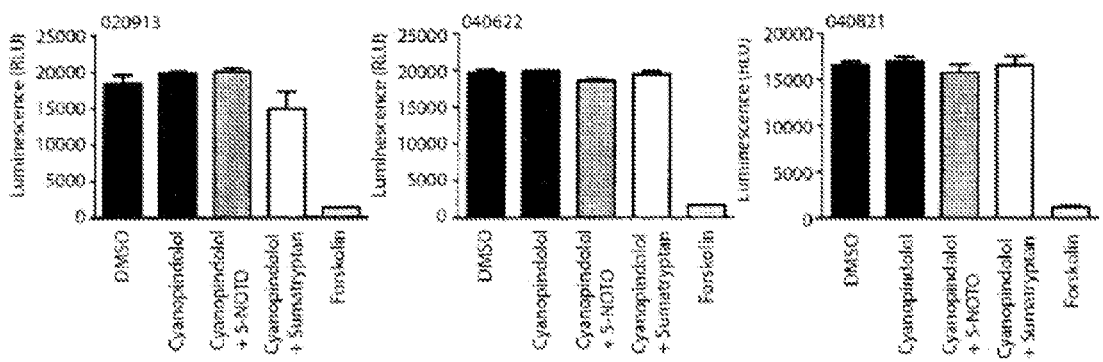
FIG. 5 depicts 5-Nonyloxytryptamine (5-NOTO) does not affect cellular cAMP levels. cAMP levels were quantitated using Promega's cAMP GLO assay kit according to manufacturer instructions. In this assay cAMP levels are inversely correlated with luminescence (RLU). Cyanopindolol is a Gα antagonist and is required for detection of 5HTR1B activity. Sumatriptan, another 5HTR1B agonist (similar to 5-NOTO), and forskolin {a known Gα agonist) were used as controls.

The Serotonin Receptors 5HTR1B and 5HTR1A are Not the Target Of 5-NOTO Action in GBM. 5-NOTO is not an FDA approved drug but its biological target is known. 5-NOTO is a specific agonist for the 5HTR1B serotonin receptor (400 times more specific for 5HTR1B then for 5HTR1A). 5HTR1B (as well as other 5HTR1 isoforms) are heterotrimeric G-protein coupled receptors which interact with Gα an inhibitor of adenylate cyclase. Therefore, we sought to determine if treatment with 5-NOTO will result in decreased cellular cAMP levels as activation of Gα should inhibit adenylate cydase, the enzyme which catalyzes the conversion of ATP to cAMP. To this end, cells were treated with cyanopindolol, an antagonist of 5HTR1B, which should increase adenylate cyclase activity (if 5HTR1B is functional), and either 5-NOTO or sumatriptan, the latter being similar to 5-NOTO, activating both 5HTR1B and 5HTR1A. As shown in FIG. 5, cAMP levels were not affected by Cyanopindolol nor were they affected by 5-NOTO, suggesting that 5HTR1B and Ga, may not play a significant role in modulating cellular cAMP levels in the three GBM neurosphere lines tested. Importantly, sumatriptan also had no effect on cellular cAMP levels, strengthening the notion that 5HTR1B (and likely 5HTR1A) have very little to no effect on cellular cAMP levels in the GBM models. In contrast, Forskolin, a known Gα agonist (an activator of adenylate cyclase), increased cellular cAMP levels dramatically and significantly, serving as a positive control for the assay. Taken together, these observations show that 5-NOTO works independent of 5HTR1B in inhibition of cell growth.

Example 6

Figure 6:
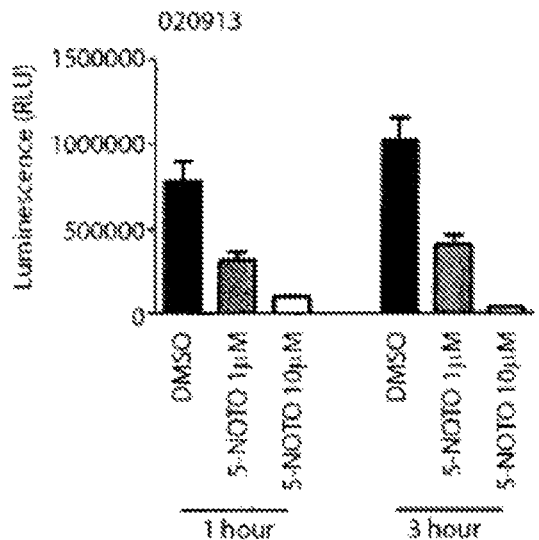
FIG. 6 shows that 5-NOTO depletes cellular ATP levels in a time and dose dependent fashion. Cells were incubated for either 1 or 3 hours in the presence of DMSO (control) or 5-NOTO (1 μM and 10 μM), ATP levels were determined using ATPlite Luminescence Assay System (PerkinElmer) according to manufacturer instructions.

5-NOTO Induces Rapid Necrosis in GBM Neurospheres. One of the classical features of necrotic cells is rapid and significant drop in intracellular ATP levels. The effect of 5-NOTO on ATP release was assayed at 1 hr and 3 hr post-treatment as follows. Briefly, 020913 neurospheres were triturated to a single-cell suspension and 20,000 cells were plated per well. Cells were plated in triplicates for vehicle alone, 1 μM 5-NOTO, and 10 μM 5-NOTO. At each time point, 100 μl of ATPlite 1-step reagent (Perkin Elmer) was added to each well and incubated with shaking for 2 minutes. After dark adaptation for 10 minutes, the samples were read using a microplate reader (Perkin Elmer). Readings were averaged and the percent differences in ATP release between treated and vehicle alone were calculated (RLU). This experiment was performed in triplicate with similar results (FIG. 6).

Example 7

Figure 4:
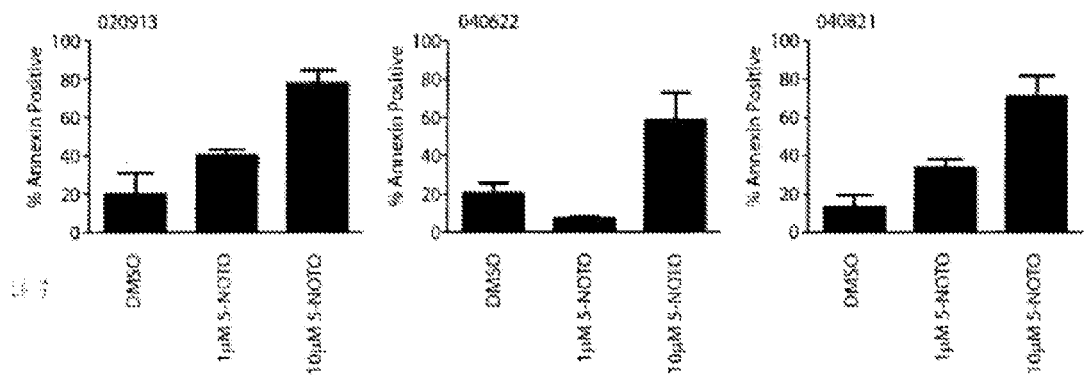
FIG. 4 depicts apoptosis analysis for GBM neurospheres treated with 5-NOTO for 24 hours. Cells were plated and then treated for 24 hours with DMSO (control), 1 μM and 10 μM 5-NOTO. Cells were then processed for Annexin V assay using the Nexin reagent (Millipore) and % Annexin positive cells was determined using flow cytometry.
Figure 7:
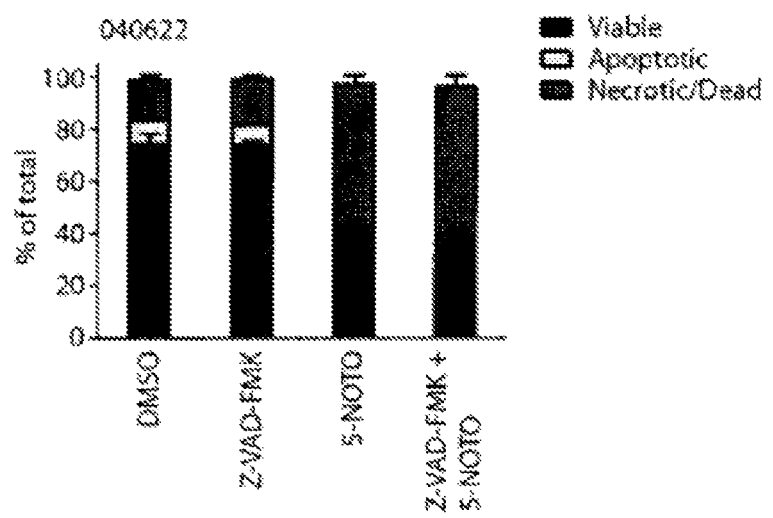
FIG. 7 shows that 5-NOTO induced cell death is primarily due to necrosis. Cells were treated with DMSO (control), the multi caspase inhibitor Z-VAD-FMK (20 μM), 5-NOTO (10 μM) or the latter two in combination. Guava Nexin assay reagent was used to determine Viable (black), apoptotic (yellow), and necrotic/apoptotic (Red) cell fractions.

To test necrotic cell death directly, cells were treated with DMSO (control) or 10 μM 5-NOTO for 30 minutes followed by apoptosis/necrosis evaluation using Guava PCA flow cytometer and Nexin reagent (Millipore). Surprisingly, 30 minutes treatment with 10 μM 5-NOTO was sufficient to increase the necrotic/dead fraction from 15.83% to 54.17% in 040622 GBM neurospheres (FIG. 7). Similar results were documented for 020913 and 040821 neurospheres (not shown). To eliminate potential contamination of the necrotic cell fraction by late apoptotic cells, cells were pre-treated with the general Caspase inhibitor, Z-VAD-FMK (Promega) to inhibit apoptotic cell death Inhibition of apoptotic cell death by Z-VAD-FMK had no effect on the necrotic/dead cell fraction, suggesting that 5-NOTO induces cellular necrosis at the early time point (minutes) while apoptosis is induced later (24 hours and beyond as shown in FIG. 4). It is important to point out that these data are in complete agreement with the dramatic drop in ATP seen at one and three hours post 5-NOTO treatment.

Example 8

Figure 8:
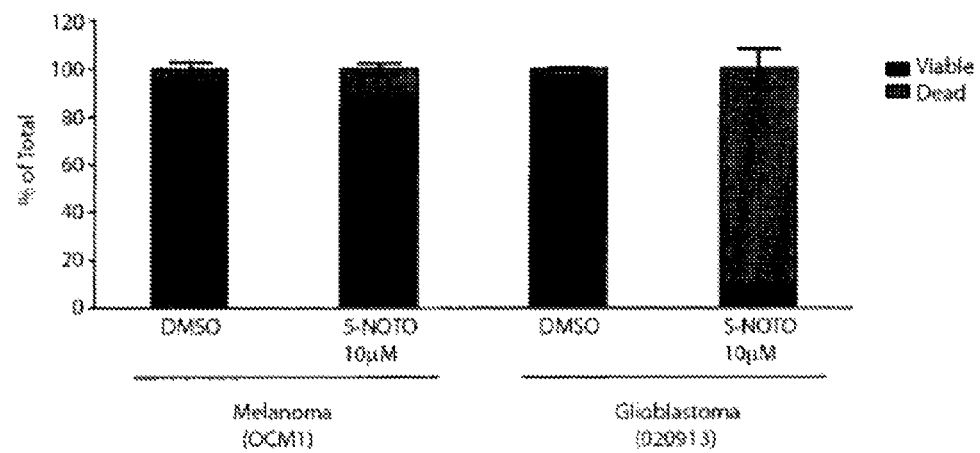
FIG. 8 shows that 5-NOTO reduces cell viability in the GBM-derived neurosphere line 020913 but not in the Uveal melanoma cell line OCM1. Cells were plated in 24-well plates and treated with DMSO or t 10 μM 5-NOTO. 48 hours later, cell viability was determined using Guava PCA flow cytometer with Guava ViaCount reagent.

We next sought to examine if 5-NOTO is generally cytotoxic or if its cytotoxicity may be specific to some cancer types. To this end, we examined the apoptotic induction in a uveal melanoma cell line, OCM 1. Cells were treated for 48 hours with 10 μM of 5-NOTO followed by Viacount assay. 5-NOTO had no effect on viability of OCM1 as the percentage of viable cells remained greater than 90% (FIG. 8). In contrast, percent viability in 020913 neurospheres treated with 10 μM 5-NOTO was only 10%. These results strongly suggest that 5-NOTO is specific for GBM and not generally cytotoxic.

Example 9

Figure 9:
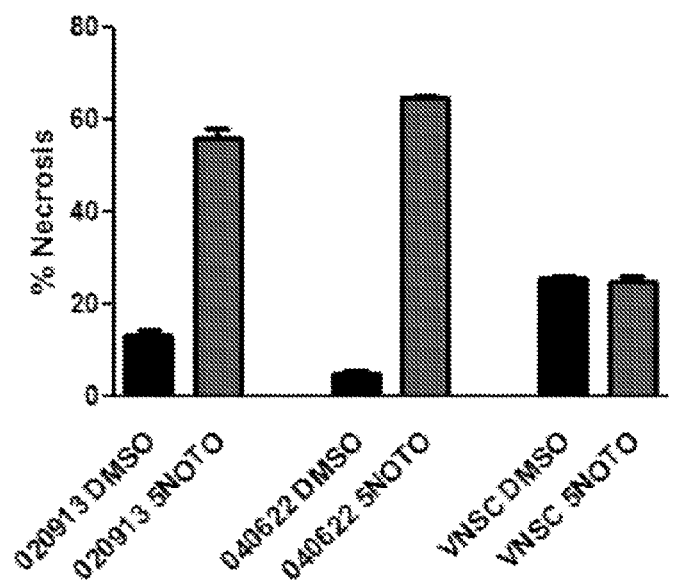
FIG. 9 depicts induction of necrotic cell death by 5-NOTO. GBM neurospheres 020913 and 040622 and normal neural stem cells immortalized with v-Myc (VNSC) were treated with DMSO (control, black bars) or with 10 μM 5-NOTO (red bars). Cells were treated for 90 minutes and then processed for viability assay using Nexin staining % Necrosis was determined by flow cytometry. 020913 and 040622 showed 56% and 65% necrosis respectively (as compared to 13% and 5% for DMSO treated cells). VNSCs on the other hand were completely resistant to 5-NOTO showing 26% and 25% in DMSO and 5-NOTO treatments, respectively. These results suggest that 5-NOTO is specific to GBM and does not affect normal neural stem cells, an important requirement for an effective therapy.

Induction of Necrotic Cell Death by 5-NOTO. GBM neurospheres 020913 and 040622 and normal neural stem cells immortalized with v-Myc (VNSC) were treated with DMSO (control, black bars) or with 10 μM 5-NOTO. Cells were treated for 90 minutes and then processed for viability assay using Nexin staining % Necrosis was determined by flow cytometry. 020913 and 040622 showed 56% and 65% necrosis respectively (as compared to 13% and 5% for DMSO treated cells). VNSCs on the other hand were completely resistant to 5-NOTO showing 26% and 25% in DMSO and 5-NOTO treatments, respectively. These results suggest that 5-NOTO is specific to GBM and does not affect normal neural stem cells, an important requirement for an effective therapy (FIG. 9).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or clearly contradicted by context.

The invention claimed is:

1. A method for lowering intracellular pH in a cell or population of cells from a subject comprising contacting the cell or population of cells with a therapeutically effective amount of a compound of formula I:

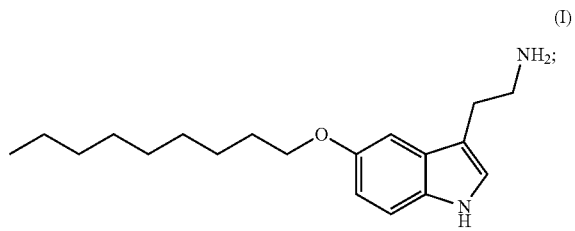 [SMILES: CCCCCCCCCOc1ccc2[nH]cc(CCN)c2c1]

or a pharmaceutically acceptable salt, solvate, or stereoisomer thereof wherein the cell or population of cells is a cell of glioblastoma.

2. A method for inducing apoptosis in a cell or population of cells from a subject comprising contacting the cell or population of cells with a therapeutically effective amount of a compound of formula I:

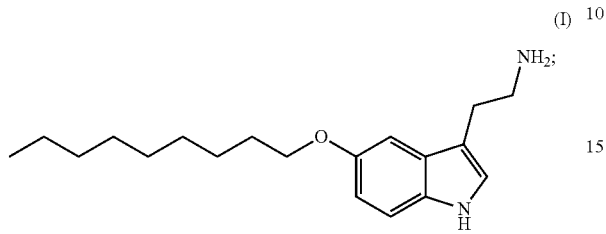

or a pharmaceutically acceptable salt, solvate, or stereoisomer thereof wherein the cell or population of cells is a cell of glioblastoma.

3. The method of claim 2, further comprising administering at least one additional chemotherapeutic compound.

4. A method for treating cancer in a subject comprising administering to the subject a therapeutically effective amount of a compound of formula I:

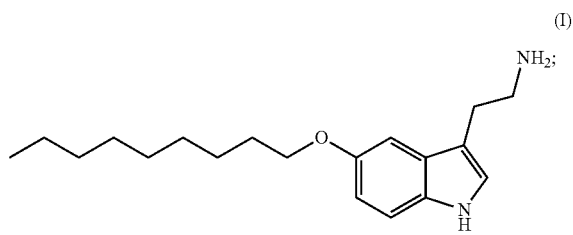 [SMILES: CCCCCCCCCOc1ccc2[nH]cc(CCN)c2c1]

or a pharmaceutically acceptable salt, solvate, or stereoisomer thereof wherein the cancer is glioblastoma.

5. The method of claim 4, further comprising administering at least one additional chemotherapeutic compound.

6. The method of claim 5, wherein the at least one additional chemotherapeutic compound is selected from the group consisting of: carmustine, lomustine, vincristine, procarbazine, carboplatin, etoposide, irinotecan, and temozoloamide.

* * * * *